United States Patent [19]

Vollhardt et al.

[11] 4,183,864

[45] Jan. 15, 1980

[54] COBALT CATALYZED STEROID SYNTHESIS

[75] Inventors: K. Peter C. Vollhardt; Raymond L. Funk, both of Berkeley, Calif.

[73] Assignee: The United States of America as represented by the Department of Health, Education and Welfare, Washington, D.C.

[21] Appl. No.: 879,492

[22] Filed: Feb. 21, 1978

[51] Int. Cl.$^2$ ................................................ C07J 1/00
[52] U.S. Cl. ................................................ 260/397.3
[58] Field of Search ................................. 260/397.3

[56] References Cited

PUBLICATIONS

Funk and Vollhardt, J. Am. Chem. Society, 98:6755 (1976).
Vollhardt, Accounts of Chemical Research, 10, 1–8 (1977).
Kametani et al., J. Am. Chem. Society, 98:11, May 26, 1976, pp. 3378–3379.
Kametani et al., J. Am. Chem. Society, 99:10, May 11, 1977, pp. 3461–3466.
Funk and Vollhardt, J. of the Chem. Society Chemical Communications, 1976, pp. 833–834.
Hillard and Vollhardt, Angew, Chem. Int. Ed. Engl., 16 (1977), No. 6, p. 399.
Hillard and Vollhardt, J. Am. Chem. Society, 99:4058, Jun. 8, 1977.
Aalbersberg et al., J. Am. Chem. Society, 97:5600, Sep. 17, 1975.
Funk and Vollhardt, J. Am. Chem. Society, 99:5483–5484 (1977).
Chemical and Engineering News, Aug. 15, 1977, p. 21.

*Primary Examiner*—Alan L. Rotman
*Assistant Examiner*—Robert C. Whittenbaugh
*Attorney, Agent, or Firm*—John S. Roberts, Jr.

[57] ABSTRACT

Steroid compounds obtained by co-oligomerization of a side chain functionalized 1,5-hexadiyne with bis(trimethylsilyl)acetylene catalyzed by cyclopentadiene cobalt dicarbonyl, $CpCO(CO)_2$, via intermediate benzocyclobutene formation followed by intramolecular cycloaddition to the sterospecific formation of the steroid nucleus. This constitutes a short steroid synthesis, five steps from commercially available acyclic precursor 1,5-hexadiyne and three steps from 2-methyl-cyclopent-2-enone.

3 Claims, No Drawings

COBALT CATALYZED STEROID SYNTHESIS

The present invention has as a target the synthesis of a steroid nucleus by means of a limited number of steps from simple reactants. As general prior art of the process, there has been recently reported a related cobalt catalyzed one-step synthesis of tricyclic ring systems B via co-oligomerization of diynes A with bis(trimethylsilyl)acetylene (BTMSA) in the presence of CpCo(CO)$_2$ (cf Scheme 1 below) and the following:

Funk and Vollhardt, "In Situ Generation and Intramolecular Trapping of o-Xylylenes by Cobalt-Catalyzed Acetylene Co-oligomerizations. A One-Step Synthesis of Polycycles," *J. Am. Chem. Society*, 98:6755 (1976).

Vollhardt, "Transition-Metal-Catalyzed Acetylene Cyclizations in Organic Synthesis," *Accounts of Chemical Research*, 10, 1–8 (1977).

In this prior art reaction five new carbon-carbon bonds are formed with control of stereochemistry to result in a preview of the ABC ring of the steroid moiety. A resume of this reaction scheme is set out below as Scheme I:

ADDITIONAL PRIOR ART STATEMENT

Kametani et al, "A Formal Regio- and Stereoselective Total Synthesis of Estrone. A Convenient Synthesis of D-Homoestrone," *J. Am. Chem. Society*, 98:11, May 26, 1976, pages 3378–3379.

Kametani et al, "A Stereoselective Total Synthesis of Estrone by an Intramolecular Cycloaddition Reaction of Olefinic o-Quinodimethane," *J. Am. Chem. Society*, 99:10, May 11, 1977, pages 3461–3466.

Funk and Vollhardt, "Hexa-1,5-diyn-3-ol Ethers as Tetramethynyl Synthons in Cobalt-Catalysed Acetylene Co-oligomerisations; a One-step Synthesis of 2,3,6,7,-Tetrakistrimethylsilylnaphthalene," *J. of the Chem. Society Chemical Communications*, 1976, pages 833–834.

Hillard and Vollhardt, "3,4-Bis(trimethylsilyl)benzocyclobutene—Synthesis of Acetylene Cotrimerization and Conversion into 1,2-Dihydrocyclobuta[c]benzyne," *Angew. Chem. Int. Ed. Engl.* 16 (1977) No. 6, page 399.

Hillard and Vollhardt, "Substituted Benzocyclobutenes, Indans, and Tetralins via Cobalt-Catalyzed Cooligomerization of α,ω-Diynes with Substituted Acetylenes. Formation and Synthetic Utility of Trimethylsilylated Benzocycloalkenes," *J. Am. Chem. Society*, 99:4058, June 8, 1977.

Aalbersberg et al, "Transition Metal Catalyzed Acetylene Cyclizations. 4,5-Bis(trimethylsilyl)benzocyclobutene, a Highly Strained, Versatile Synthetic Intermediate," *J. Am. Chem. Society*, 97:5600, Sept. 17, 1975.

Funk and Vollhardt, "A Cobalt-Catalyzed Steroid Synthesis," *J. Am. Chem Society*, 99:5483 (1977).

In the present invention, which is outlined below in Scheme II, adaptation has been made for the synthesis of the crucial 1,5-hexadiyne precursor 6.

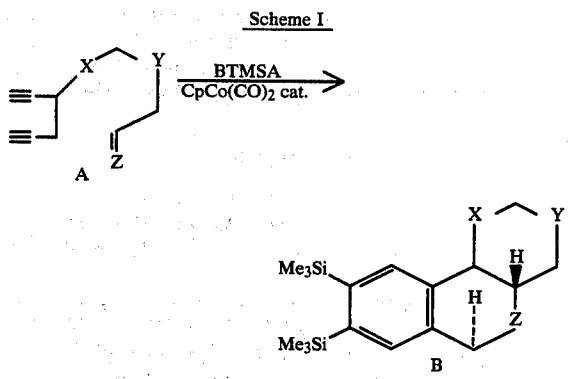

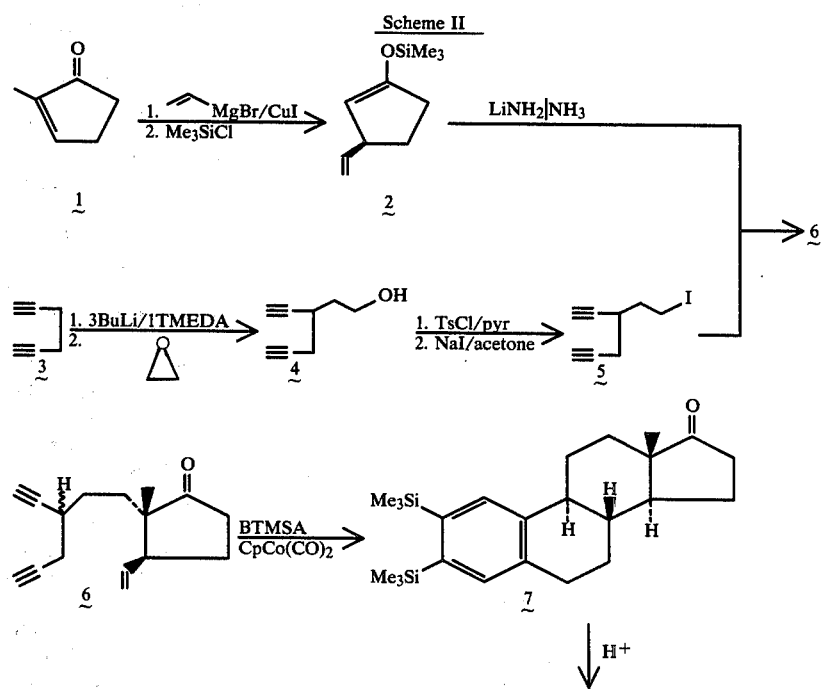

Scheme II

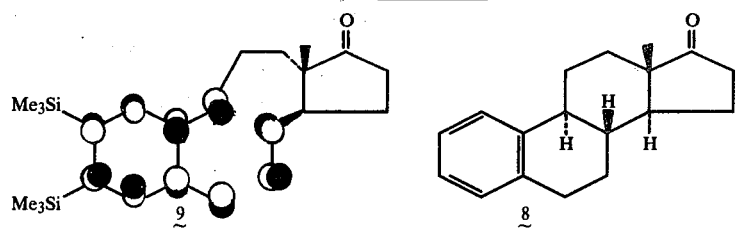

2-Methylcyclopent-2-enone (1), when treated with vinylmagnesium bromide (CuI, THF; −60° to −40°; 45 min) followed by addition of trimethylsilylchloride (HMPA, Et₃N, −40° to room temp, 30 min) gave the enol ether 2 in 89% yield. In a parallel line of experiments the precursor, 1,5-hexadiyne (3) was converted to alcohol (4) by alkylation of the 1,5-hexadiyne trianion in the presence of three equivalents of BuLi and one equivalent of tetramethylethylenediamine (TMEDA) with one equivalent $\underline{1}$. Diynol 4 was quantitatively converted to the corresponding p-toluenesulfonate (TsCl, pyridine; 0° C.; 14 h), which, on exposure to Finkelstein conditions (45° C.; 30 h), gave iodide 5 in 96% yield. The regiospecific enolate generated from 2 (LiNH₂, NH₃ liq., THF; 30 min) was stereospecifically alkylated with three equivalents of 5 to give after column chromatography (silica) 64% diynenone 6 as a mixture of diastereomers in addition to 1.9 equivalent recovered of 5. This reaction establishes the desired stereochemistry around what is to become the trans-CD-ring junction of the steroid nucleus. Mixture 6 was separable by chromatography but on cyclization and conrotatory outward benzocyclobutene ring opening, both diastereomers were expected to and gave the same o-xylylene intermediate 9. The co-oligomerization of 6 with BTMSA (solvent) in the presence of catalytic (5 mol %) amounts of CpCo(CO)₂ under oxygen-free conditions using syringe pump techniques (35 h addition time) followed by continued heating gave as a product racemic 2,3-bis(trimethylsilyl)-estra-1,3,5(10)trien-17-one (7) in 71% yield as colorless crystals. Shorter reaction times allowed the isolation of the two diastereomeric benzocyclobutene intermediates 10, separated by column chromatography on silica. Slow addition of 10 to refluxing decane under N₂ cleanly gave 7.

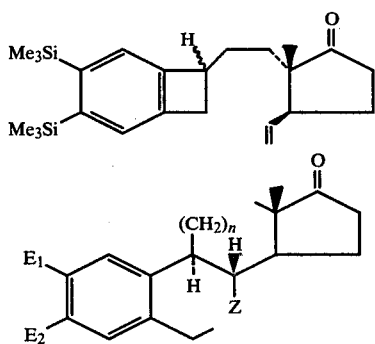

Chemical structural proof for 7 was obtained by quantitative protodesilylation of estra-1,3,5(10)-trien-17-one (8) (CF₃COOH—CCl₄-ether, 10:10:1; room temperature; 20 h) identical (TLC R$_f$, IR, ¹H—NMR, ¹³C—NMR, m/e) with an authentic sample of d-estratrienone.

The stereospecificity observed in the 6→7 transformation is remarkable. The desired trans-anti-trans geometrical arrangement in 7 is obtained rather than the trans-syn-trans form and the favorable preference may be due to steric considerations.

The described approach constituted a short synthesis of the steroid nucleus from an acyclic precursor and a yield of 28% overall from commercially available 1,5-hexadiyne (3) and 40% from 2-methylcyclopent-2-enone (1) has been achieved. The present invention may be utilized to produce new 7-azaestratriene derivatives, C norsteroids, and synthetically useful 11-hydroxy and A-ring aza analogs as well as new compounds achieved by incorporating the tetrahydroisoquinoline moiety into the steroid moiety.

EXAMPLE

Under similar conditions following Scheme II of the specification, another example was utilized in the laboratory for the synthesis of the crucial 1,5-hexadiyne precursor 6.

2-Methylcyclopent-2-enone (1), when treated with vinylmagnesium bromide (CuI, THF; −60° to −40°; 45 min) followed by addition of trimethylsilylchloride (HMPA, Et₃N, −40° to room temp, 30 min) gave the enol ether 2 in 85% yield. In parallel experiments diyne-ol 4 was quantitatively converted to the corresponding p-toluene sulfonate (TsCl, pyridine, 0°, 14 h) which, on exposure to Finkelstein conditions (NaI, acetone, 45°, 30 h), gave iodide 5 in 84% yield. The regiospecific enolate generated from 2 (LiNH₂, NH₃ liq., THF, 30 min) was stereospecifically alkylated with two equivalents of 5 to give after column chromatography (silica) ca. 50% of diyneenone 6 as a mixture of diastereomers in addition to 87% recovered excess 5. Although separable by chromatography, this mixture was reacted further as such since on cyclization and conrotatory outward benzocyclobutene ring opening, both diastereomers were expected to give the same o-xylylene intermediate (e.g., 9). Co-oligomerization of 6 with BTMSA (solvent) in the presence of catalytic (5 mol %) amounts of CpCo(CO)₂ under oxygen free conditions using syringe pump techniques (35h addition time) followed by continued heating gave racemic 2,3-bis(trimethylsilyl)-estra-1,3,5(10)-triene-17-one (7) in 71% yield as colorless crystals. Shorter reaction times allowed the isolation of the two diastereomeric benzocyclobutene intermediates 10, separated by column chromatography on silica. Slow addition of 10 to refluxing decane under N₂ cleanly gave 7. Chemical structural proof for 7 was obtained by quantitative protodesilylation to estra-1,3,5(10)-triene-17-one (8) (CF₃COOH—CCl₄-ether, 10:10:1, room temp., 20H) identical (tlc-R$_f$, IR, $^1$H—NMR, $^{13}$C—NMR, m/e) with an authentic sample of d-estratrienone.

This example showed 20% overall yield from commercially available 1,5-hexadiyne (3) and 30% from 2-methylcyclopent-2-enone (1).

We claim:

1. A method of synthesizing the steroid 4-ring system which comprises reacting

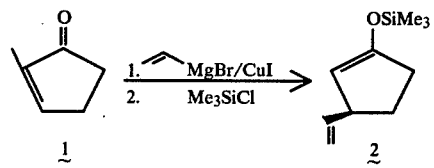

and simultaneously utilizing

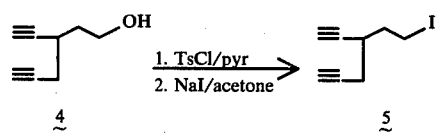

and reacting

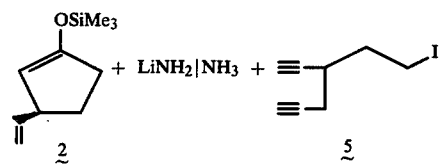

to give

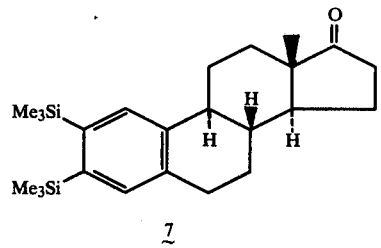

which is then reacted with BTMSA/CpCo(CO)$_2$ to give

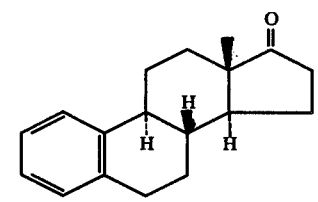

which is treated with an acid to give

2. The method of claim 1 wherein 7 is a racemic 2,3-bis(trimethylsilyl)-estra-1,3,5(10)-triene-17-one.

3. The method according to claim 1 wherein 8 is estra-1,3,5(10)-triene-17-one.

* * * * *

UNITED STATES PATENT OFFICE
CERTIFICATE OF CORRECTION

Patent No. 4,183,864    Dated January 15, 1980

Inventor(s) K. Peter C. Vollhardt and Raymond L. Funk

It is certified that error appears in the above-identified patent and that said Letters Patent are hereby corrected as shown below:

Column 1, line 35, Compound B should be:

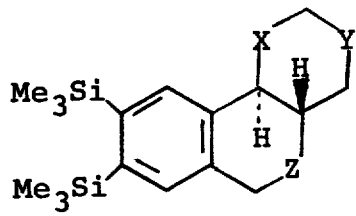

B

Signed and Sealed this

Tenth Day of June 1980

[SEAL]

Attest:

SIDNEY A. DIAMOND

Attesting Officer

Commissioner of Patents and Trademarks